United States Patent
Akiyama et al.

(10) Patent No.: US 6,947,793 B2
(45) Date of Patent: Sep. 20, 2005

(54) ELECTROTHERAPY APPARATUS AND ITS ELECTRIC ENERGY DELIVERING METHOD

(75) Inventors: Naoto Akiyama, Tokyo (JP); Masahiko Inomata, Tokyo (JP); Ikuhiro Tsumura, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 51 days.

(21) Appl. No.: 09/800,788

(22) Filed: Mar. 8, 2001

(65) Prior Publication Data

US 2002/0022867 A1 Feb. 21, 2002

(30) Foreign Application Priority Data

Mar. 8, 2000 (JP) ........................................ 2000-062942

(51) Int. Cl.[7] .............................................. A61N 1/362
(52) U.S. Cl. ........................................................ 607/5
(58) Field of Search ............................... 600/509; 607/4, 607/5, 7, 9, 11, 74

(56) References Cited

U.S. PATENT DOCUMENTS 5,222,492 A * 6/1993 Morgan et al. ......... 128/419 D
5,607,454 A * 3/1997 Cameron et al. ............... 607/5
6,405,081 B1 * 6/2002 Lyster et al. .................... 607/5

* cited by examiner

Primary Examiner—Jeffrey R. Jastrzab
Assistant Examiner—Frances P. Oropeza
(74) Attorney, Agent, or Firm—Sughrue Mion, PLLC

(57) ABSTRACT

An electrotherapy apparatus for generating first and second waveforms having reversed polarities. When the waveform of the electric energy outputted from the output electrodes 112a and 112b is the positive phase, the inductor 105, electric energy storage section 104, the first switch means 101, output electrode 112a, patient 113, and the output electrode 112b are connected so that these can form the closed circuit. In the case where the waveform of the electric energy outputted from the output electrodes 112a and 112b is the negative phase, when the first switch means 101 is closed, the inductor 105 and the electric energy storage section 104 form the closed circuit, and when the first switch means 101 is opened, the inductor 105 and the electric energy storage section 104 are electrically separated, and the delivery of the electric energy to the output electrodes 112a and 112b is conducted by the inductor 105.

14 Claims, 8 Drawing Sheets

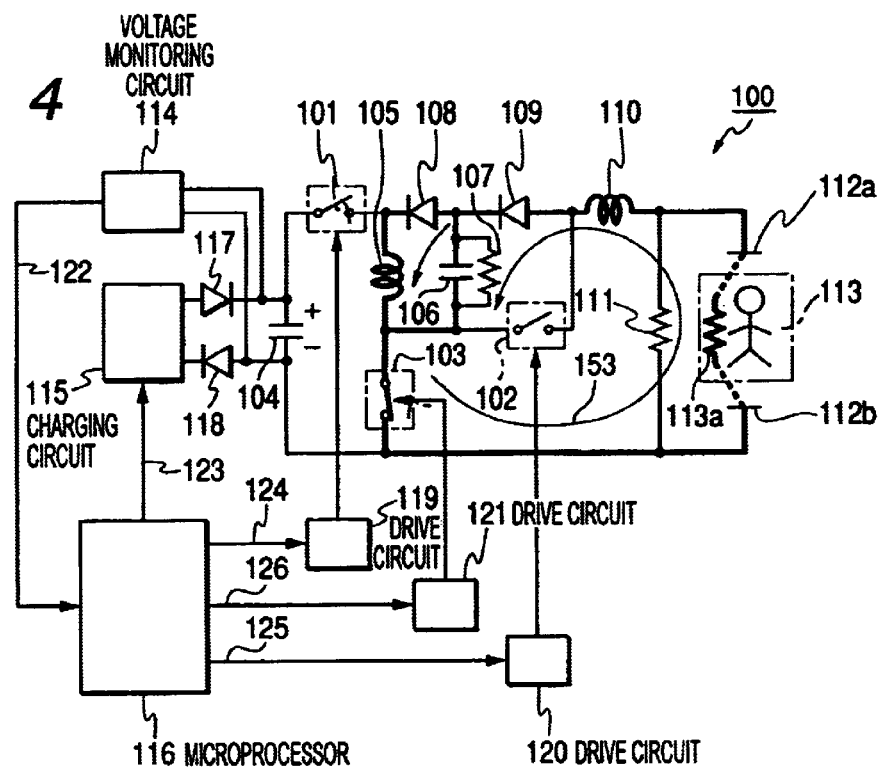
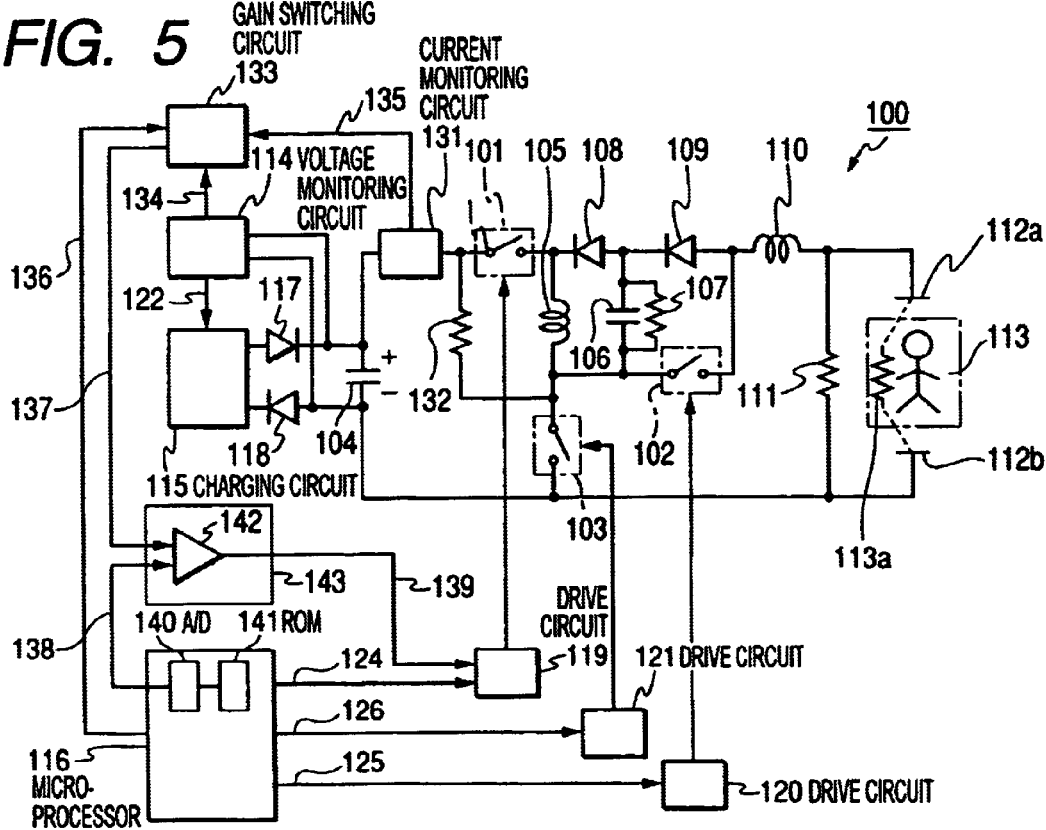

ELECTROTHERAPY APPARATUS AND ITS ELECTRIC ENERGY DELIVERING METHOD

BACKGROUND OF INVENTION

1. Field of Invention

The present invention relates to an internal and external electrotherapy apparatus to apply an electric stimulation pulse onto the patient and its electric energy delivering method, and specifically to an electrotherapy apparatus effective in terminating the fibrillation of hearts in cardiac diseases, and its electric energy delivering method.

2. Related Art

In patients having cardiac diseases, the fibrillation is an important factor which causes the patient' death. In order to terminate the fibrillation, an electrotherapy apparatus (called defibrillator) which applies a shock by an electric stimulation pulse (called defibrillation pulse) onto the heart of the patient and terminates the fibrillation, is commonly used.

The internal defibrillator is adjusted and used for only an individual patient, therefore, because the impedance between electrodes is a value inherent to the patient and almost constant, the waveform can be adjusted so that the defibrillation efficiency becomes optimum for the impedance of the patient. On the other hand, in the external defibrillator, the higher current output than that of the internal type is necessary, and further, because the impedance is used for various unspecified patients, when the fibrillation is not terminated by the first electric shock, a method of delivering shock again with the increased energy value is applied.

Further, as the waveform, there are a monophasic type and a biphasic type, and recently, the biphasic type in the both is known to have advantages that the output electric energy may be smaller than that of the monophasic type, the energy efficiency is high, and the damage to the patient is small.

Referring to the drawing, an output circuit of the conventional biphasic defibrillator will be described below. FIG. 10 is a view for explaining the output circuit of the conventional biphasic defibrillator, and FIG. 11 is a view of its waveform.

FIG. 10(*a*) is an example in which a mechanism to reverse the phase by four switches is provided, and the mechanism has a capacitor 201 to store the electric energy, switches 202, 203, 204, and 205, and output electrodes 206*a*, and 206*b*. This is the technology disclosed in U.S. Pat. No. 4,850,357 (JP-B-4-45193).

In this biphasic defibrillator, when the first phase (positive phase) waveform electric pulse is outputted, the switches 202 and 205 are turned on, and switches 203 and 204 are turned off, and thereby, the positive polarity voltage of the capacitor 201 is applied on the output electrode 206*a*, and the negative polarity voltage of the capacitor 201 is applied on the output electrode 206*b*, and from these electrodes, the positive phase truncated exponential waveform electric pulse is applied to the patient 207 (impedance of the patient: 207*a*). Then, when the voltage or time comes to a predetermined value, the switches 202 and 205 are turned off.

Next, in the case where the second phase (negative phase) waveform electric pulse is outputted, when the switches 203 and 204 are turned on, the negative polarity voltage of the capacitor 201 is applied onto the output electrode 206*a*, and the positive polarity voltage of the capacitor 201 is applied onto the output electrode 206*b*, and from these electrodes, the negative phase truncated exponential waveform electric pulse is applied onto the patient 207. Then, when the voltage or time comes to a predetermined value, the switches 203 and 204 are turned off.

According to that, from the output circuit of the above conventional biphasic defibrillator, the truncated exponential biphasic waveform as shown in FIG. 11(*a*) can be obtained.

Further, FIG. 10(*b*) is an example in which a mechanism to reverse the phase by 2 capacitors is provided, and the mechanism has capacitors 211 and 212 to store the electric energy, switches 213 and 214, and output electrodes 215*a* and 215*b*. This is a technology disclosed in the U.S. Pat. No. 5,871,505.

In the biphasic defibrillator, in the case where the first phase (positive phase) waveform electric pulse is outputted, when the switch 213 is turned on, and the switch 214 is turned off, the positive polarity voltage of the capacitor 211 is applied onto the output electrode 215*a*, and the negative polarity voltage of the capacitor 211 is applied onto the output electrode 215*b*, and from these electrodes, the first phase (positive phase) truncated exponential waveform electric pulse is applied onto the patient 216 (the impedance of the patient: 216*a*).

Then, when the voltage or time comes to a predetermined value, the switch 213 is turned off.

Next, when the second phase (negative phase) waveform electric pulse is outputted, the switch 214 is turned on, and the switch 213 is turned off, thereby, the negative polarity voltage of the capacitor 212 is applied onto the output electrode 215*a*, and the positive polarity voltage of the capacitor 212 is applied onto the output electrode 215*b*, and from these electrodes, the second phase (negative phase) waveform electric pulse is applied onto the patient 216.

It According to that, the biphasic waveform as shown in FIG. 11(*b*) is obtained from the output circuit of the above conventional biphasic defibrillator.

A publicly known example disclosed in the U.S. Pat. No. 5,591,209 is for the implantable defibrillator, and a method in which the first phase applies the energy stored inhigh voltage storage capacitors onto the heart, and the second phase directly applies the energy from the battery source in low voltage onto the heart, is shown.

In the technology of the implantable defibrillator having the low output energy disclosed in the U.S. Pat. No. 5,350,403 (JP-A-6-47100), a control unit is provided between a charging capacitor and the electrode, and by turning on or off the circuit, the electric pulse having a predetermined current curve is applied onto the patient.

The U.S. Pat. No. 5,607,454 (JP-A-9-500309) uses the truncated exponential curve. With this method, the durations of the waveforms of the first phase and the second phase are changed depending on the impedance of the patient.

Comparing to the monophasic defibrillator, the conventional biphasic type defibrillator, for example, in the case of FIG. 10(*a*), 4 switches are necessary, and further, in the case of FIG. 10(*b*), 2 electric energy storage section (capacitor) are necessary, and the number of elements is increased as compared to the monophasic defibrillator.

Generally, in the defibrillator, in order to generate the high voltage from the low voltage power source such as a battery, even when the number of the electric energy storage sections (capacitor) and switches (structured by superimposing a plurality of stages of semiconductor switches) is increased by, for example, only one, the apparatus becomes larger and heavier, therefore, problems that the portability in the emergency circumstances is lowered, or the like, are caused, and further, the cost of the overall apparatus is also increased.

In the output system of the conventional truncated exponential waveform as disclosed in the U.S. Pat. No. 5,607,454 (JP-W-9-500309), the impedance of the patient directly influences the decay of the voltage of the capacitor, and the time constant is unconditionally determined, and as the control to form the waveform, it can operate only when the waveform output is completed (truncated).

Further, in the external defibrillator, because the electric stimulation pulse is applied transthoracically, the impedance applied across output electrodes during operation is different depending on the patient (inherency), and further, the large difference is generated depending on the physical and physiological difference of the patient.

Further, in the following references 1 and 2, when the time period in which the electric pulse is applied, is not within a predetermined time period, the effective defibrillation can not be carried out.

Reference 1: Koning G. Schneider H. Hoelin A J. et al. "Amplitude-duration relation for direct ventricular defibrillation with rectangular pulses." Medical & Biological Engineering, 1975 May: on page 388–395.

Reference 2: "Ventricular Defibrillation Using Biphasic Waveforms: The Importance of Phasic Duration" JACC 1989 January 13:1 207–14.

Accordingly, when the sufficient electric energy can not be delivered within this effective period, even when the electric pulse is continuously applied over this period, there is a problem that the effect of the defibrillation can not be increased.

Accordingly, when the impedance of the patient is high, because only by the output of the conventional truncated exponential waveform, it takes a lot of time to deliver the electric energy to the patient, the sufficient energy can not be delivered within the effective period to apply the defibrillation pulse, and therefore it unavoidably truncates the output of the defibrillation pulse.

Further, in the technology disclosed in the U.S. Pat. No. 5,591,209, the energy stored in the high voltage storage capacitors is used only for the first phase waveform. Accordingly, all the energy stored in the capacitors is not used for the defibrillation.

That is, in such the waveform, because the first phase is completed under the condition that the voltage of the capacitors is lowered to about 40%, it comes to an account that about 16% of overall amount of the energy stored in the capacitors are not used for the defibrillation.

In the external defibrillator, normally, it is necessary that the safety is secured by electrically isolating the circuit passing through the low voltage power source and the patient, (for example, some measures to isolate the patient at the time of the second phase output is provided), however, it is not disclosed in the above publicly known examples.

Further, when the technology in the above publicly known examples is applied for the external defibrillator, it is additionally necessary to provide the insulation circuit composed of transformer, or the like, to output the second phase other than the insulation transformer to store the energy in the energy storage section, and it is not preferable from the viewpoint of the size reduction to apply it for the external type.

Further, because the power source of the second phase is directly applied from the power source apparatus (battery source), the instantaneous maximum electric power applied on the patient is limited by the maximum electric power of the power source apparatus.

When such the system is applied for the external defibrillator, because the very large instantaneous electric power is required as compared to that of the internal defibrillator, when the capacity of the power source is not designed to be large, the effective defibrillation pulse can not be outputted. Generally, the inherency of the impedance value of the patient spreads to the range from 25 Ω to 125 Ω.

For example, in the second phase, in order to apply the voltage of 300 V to the patient, the power source capacity P shown by the following equation 1 is required.

$$P=300\ (V)^2/25(\Omega)=3600\ (\text{Watt}) \quad (1)$$

As described above, because the very large power source capacity of 3600 (Watt) is necessary, it is difficult also from the viewpoint of the power source capacity to apply for the external defibrillation.

Further, because the power is not controlled in the second phase, the necessary energy can not always be delivered within the effective time period.

Further, in the technology disclosed in the U.S. Pat. No. 5,350,403 (JP-A-6–47100), the control unit which can turn on or turn off the circuit, is provided between the charging capacitor and electrode, and the maximum voltage value of the output waveform obtained at the time of the control can not be larger than the capacitor voltage obtained when the circuit is continuously turned on by the control unit.

This is the reason why the unit is structured such that the control unit is operated only in the direction to control the output.

Further, at the time of the defibrillation, when the impedance of the patient is large, there is a case in which it is preferable that the higher voltage than the voltage stored in the charging capacitor is supplied to the patient. In the conventional technology, in order to defibrillate in biphasic waveform, it is necessary that the 2 charging capacitors are additionally prepared, and the reverse of the polarity of the output voltage is conducted by using 4 switches (called H-bridge).

SUMMARY OF INVENTION

The present invention is attained in view of problems of the conventional technologies, and an object of the present invention is to solve the above problems, and to provide the electrotherapy apparatus which is effective in terminating the fibrillation of the heart in cardiac diseases, and its electric energy delivering method.

In order to solve the above problems, the electrotherapy apparatus according to the first aspect of the invention, has the electric energy storage section to generate the stimulation pulse, and the output electrode to apply the stimulation pulse to the patient, and is structured so that the polarity of the voltage outputted to the output electrode is reversed, and is structured such that at least the first phase waveform and the second phase waveform of the electric energy are outputted from the output electrode, and the shape of the second phase waveform of the electric energy can be controlled, thereby, the output waveform of the second phase can be freely set, without depending on the voltage (V1t) of the electric energy storage section at the time of the start of the second phase.

The electrotherapy apparatus according to the second aspect of the invention, has the electric energy storage section to generate the stimulation pulse, and the output electrode to apply the stimulation pulse to the patient, and is structured so that the polarity of the voltage outputted to the output electrode is reversed, and is structured such that at least the first phase waveform and the second phase waveform are outputted from the output electrode, and the necessary electric energy is delivered within a predetermined time period by the outputted second phase waveform of the electric energy, thereby, the predetermined electric energy can be delivered to the patient within an optimum time period for the defibrillation, without depending on the impedance of the patient.

The electrotherapy apparatus according to the third to seventh aspect of the invention, has a control means for controlling so that the electric power of the electric energy outputted from the output electrode becomes a predetermined value, without depending on the impedance of the patient, during the output period of the second phase waveform.

Further, the control means output controls so that the value relating to the voltage which is lowered corresponding to the amount of the energy supplied from the electric energy storage section, varies corresponding to the function of the predetermined time period and the value relating to the voltage.

The value relating to the voltage is the voltage, the voltage differential value, or voltage double differential value.

The control means output controls so that the value relating to the current which varies corresponding to the amount of the energy supplied from the electric energy storage section, changes corresponding to the function of the predetermined time period and the value relating to the current.

The value relating to the current is the current, the current differential value, or current double differential value.

As described above, by controlling the electric parameters relating to the energy storage section which are varied corresponding to the amount of the delivery of the electric energy, the delivering energy can be controlled.

The electrotherapy apparatus according to the eighth aspect of the invention has: a patient parameter measuring means for measuring the patient parameter; an output electrode parameter measuring means for measuring the voltage generated between the output electrodes or the current flowing to the output electrode; and a control means for controlling so that the electric power of the electric energy becomes a predetermined value without depending on the values of the patient parameters, according to the patient parameters measured before the output of the second phase waveform by the patient parameter measuring means, and to the value relating to the voltage between the output electrodes or the value relating to the current flowing to the output electrode, measured during the output of the second phase waveform, by the output electrode parameter measuring means, thereby, the electric power of the output energy can be controlled according to the patient parameter before the output of the second phase waveform, and the electric parameter on the output electrode during the output of the second phase waveform.

The electrotherapy apparatus according to the ninth aspect of the invention is structured such that: when the waveform of the electric energy outputted from the output electrode is the first phase waveform, the inductor, electric energy storage section, the first switch means, output electrode, patient and at least the other output electrode are connected so that these can form the closed circuit; and in the case where the waveform of the electric energy outputted from the output electrode is the second phase, when the first switch means is closed, the inductor and the electric energy storage section form the closed circuit in the apparatus not including the patient, and when the first switch means is opened, the inductor and the electric energy storage section are electrically separated from each other, and the electric energy to the output electrode is delivered from the inductor, thereby, the biphasic defibrillator (electrotherapy apparatus) can be structured by one electric energy storage section, and the second phase output waveform can be freely set.

The electrotherapy apparatus according to the tenth aspect of the invention is structured such that the shape of the second phase waveform can be controlled by the open/close of the first switch means, thereby, when only one switch means is opened and closed, the second phase output waveform can be freely set by the simple control method.

The electrotherapy apparatus according to the eleventh aspect of the invention has the second switch means and the third switch means to shape the first phase and the second phase of the waveform of the electric energy outputted from the output electrode, thereby, when only two switch means are opened and closed, the first phase and the second phase can be formed by the simple control means.

In the electrotherapy apparatus according to the twelfth aspect of the invention, the first switch means, the second switch means, and the third switch means are structured by the semiconductor switches, thereby, the opening and closing of each switch means can be conducted with high speed by the electric control.

The electrotherapy apparatus according to the thirteenth aspect of the invention has: the electric energy storage section to generate the stimulation pulse; the output electrode to apply the stimulation pulse to the patient; and the control means for controlling the waveform shape of the stimulation pulse so that the predetermined electric energy stored in the electric energy storage section is outputted to the output electrode through the electric circuit within a predetermined time period, thereby, by controlling the shape of the pulse waveform, the apparatus is structured so that the necessary energy can be outputted within a constant time period, thereby the effective energy can be delivered in an effective stimulation period.

In the electrotherapy apparatus according to the fourteenth aspect of the invention, when the control means controls the waveform shape of the stimulation pulse so that the electric power of the electric energy applied from the electrode becomes a predetermined value, without depending on the value of the impedance of the patient, the electric power is controlled so that it becomes a predetermined value without depending on the value of the impedance even when the impedance of the patient is low or high, thereby, the stimulation pulse having the effective energy amount can be applied within a predetermined time period.

In the electrotherapy apparatus according to the fifteenth to eighteen aspect of the invention, the control means output controls so that the value relating to the voltage which is lowered corresponding to the amount of the energy supplied from the electric energy storage section, changes corresponding to the function of the predetermined time and the value relating to the voltage.

Further, the value relating to the voltage is the voltage value, the voltage differential value, or the voltage double differential value.

The control means output controls so that the value relating to the current which varies corresponding to the amount of the energy supplied from the electric energy storage section, changes corresponding to the function of the predetermined time and the value relating to the current.

The value relating to the current is the current value, the current differential value, or the current double differential value.

According to the above, the delivering energy can be controlled by controlling the electric parameters relating to the energy storage section which are changed corresponding to the energy delivering amount.

The electrotherapy apparatus according to the ninteenth aspect of the invention has: a patient parameter measuring means for measuring the patient parameter; and an output electrode parameter measuring means for measuring the voltage generated across the output electrodes or the current flowing to the output electrode, and the control means controls so that the electric power of the electric energy becomes a predetermined value without depending on the values of the patient impedance, according to the patient parameters measured before the output of the second phase waveform by the patient parameter measuring means, and to the value relating to the voltage between the output electrodes or the value relating to the current flowing to the output electrode, measured during the output of the second phase waveform, by the output electrode parameter measuring means, thereby, the electric power of the output energy can be controlled according to the patient parameter before the output of the second phase waveform, and the electric parameter on the output electrode during the output of the second phase waveform.

The electrotherapy apparatus according to the twentieth aspect of the invention has: the electric energy storage section to generate the stimulation pulse; the output electrode to apply the stimulation pulse to the patient; and the control means for controlling the waveform shape of the stimulation pulse so that the predetermined electric energy stored in the electric energy storage section is outputted to the output electrode through the electric circuit within a predetermined time period, and the electric circuit has the switch to control the waveform shape of the stimulation pulse, and the control means operates the switch to conduct the continuous switching operation by the pulse width modulation control during a period in which the stimulation pulse is applied to the patient, thereby, by operating the switch in the electric circuit to continuously conduct the switching operation by the pulse width modulation system, the electric power can be controlled so that the necessary energy is delivered.

In the electrotherapy apparatus according to the twenty first aspect of the invention, the control means has the reference curve so that the waveform shape of the stimulation pulse is formed into the predetermined shape, thereby, by controlling according to the reference curve stored in the control means, the stimulation pulse having the predetermined shape can be applied.

In the electrotherapy apparatus according to the twenty second to the twenty third aspect of the invention, the control means controls the switching operation of the switch according to the difference between the value relating to the voltage which is lowered corresponding to the amount of the energy supplied from the electric energy storage section, and the reference curve, or the control means controls the switching operation of the switch according to the difference between the value relating to the current which varies corresponding to the amount of the energy supplied from the electric energy storage section, and the reference curve, thereby, by controlling the electric parameters relating to the energy storage section which varies corresponding to the amount of the supplied energy, according to the reference curve, the delivering energy can be controlled.

In the electrotherapy apparatus according to the twenty fourth aspect of the invention, the control means controls so that the electric power of the electric energy outputted from the output electrode becomes a predetermined value, without depending on the impedance of the patient, thereby, even when the impedance of the patient is low or high, by controlling so that the electric power becomes a predetermined value, without depending on the impedance value, the stimulation pulse having the effective amount of the energy can be applied.

The electrotherapy apparatus according to the twenty fifth aspect of the invention has: a patient parameter measuring means for measuring the patient parameter; an output electrode parameter measuring means for measuring the voltage generated between the output electrodes or the current flowing to the output electrode, and a control means controls the switching operation of the switch, according to the patient parameters measured before the output of the stimulation pulse by the patient parameter measuring means, and to the value relating to the voltage between the output electrodes or the value relating to the current flowing to the output electrode, measured during the output of the stimulation pulse, by the output electrode parameter measuring means, thereby, the electric power of the energy can be controlled according to the patient parameter before the output of the stimulation pulse and the electric parameter on the output electrode during the applying of the stimulation pulse.

In the electrotherapy apparatus according to the twenty sixth aspect of the invention, the control means controls so that the electric power of the electric energy applied from the output electrode becomes a predetermined value, thereby, even when the impedance of the patient is low or high, by controlling so that the electric power becomes a predetermined value, without depending on the impedance value, the stimulation pulse having the effective amount of the energy can be applied.

The electrotherapy apparatus according to the twenty seventh aspect of the invention has: an inductor section to store the magnetic energy to generate the stimulation pulse; the output electrode to apply the stimulation pulse to the patient; and the control means for controlling the waveform shape of the stimulation pulse so that the predetermined energy in the energy stored in the inductor section is delivered to the patient through the output electrode, thereby, because the apparatus is structured such that the electric energy is supplied to the inductor, the waveform shape of the stimulation pulse can be controlled with the high degree of freedom.

The electrotherapy apparatus according to the twenty eighth aspect of the invention has, in order to supply the energy to the inductor section, the electric energy storage section to store the energy, thereby, because the apparatus has the electric energy storage section to store the electric energy other than the inductor, a predetermined amount of the energy in the energy stored in the electric energy storage section can be supplied to the inductor.

In the electrotherapy apparatus according to the twenty ninth aspect of the invention, the electric energy storage section is a capacitor, and when the energy stored in the inductor section is supplied to the output electrode, the control means can control so that the absolute value of the output is higher than the absolute value of the voltage stored in the capacitor, thereby, because the control means controls so that the energy is supplied by the inductor, even when the patient has the high impedance, the energy can be supplied while the voltage value outputted to the output electrode is increased higher than that of the capacitor at need, which is the electric energy storage section.

In the electrotherapy apparatus according to the thirtieth aspect of the invention, the inductor section is connected to the electric energy storage section through the first switch means which can be repeatedly switched, and the control means conducts the switching control by controlling the repeated switching of the first switch means, thereby, the energy stored in the capacitor is supplied once to the inductor, and it can be supplied to the output electrode.

In the electrotherapy apparatus according to the thirty first aspect of the invention, the control means controls the switching of the first switch means by the pulse width modulation control, thereby, the electric power can be controlled.

In the electrotherapy apparatus according to the thirty second aspect of the invention, in the electrotherapy apparatus, the control means controls the waveform shape of the stimulation pulse so that the electric power of the electric energy outputted from the output electrode becomes constant without depending on the impedance of the patient, thereby, even when the impedance of the patient is low or high, by controlling so that the electric power becomes constant without depending on the impedance value, the stimulation pulse having the effective energy amount can be applied.

In the electrotherapy apparatus according to the thirty third aspect of the invention, the control means stores the reference curve in order to form the waveform shape of the stimulation pulse into the predetermined shape, thereby, by controlling according to the stored reference curve, the stimulation pulse having the predetermined shape can be applied.

In the electrotherapy apparatus according to the thirty fourth to thirty fifth aspect of the invention, the control means controls the switching operation of the switch according to the difference between the value relating to the voltage which is lowered corresponding to the energy amount supplied from the electric energy storage section, and the reference curve, and further, the control means controls the switching operation of the switch according to the difference between the value relating to the current which varies corresponding to the energy amount supplied from the electric energy storage section, and the reference curve, thereby, by controlling the electric parameters relating to the energy storage section which varies corresponding to the energy supply amount according to the reference curve, the supply energy can be controlled.

The electrotherapy apparatus according to the thirty sixth aspect of the invention has a charging circuit to charge the electric energy storage section, thereby, when the energy is consumed by the use, the apparatus can be used again.

In the electrotherapy apparatus according to the thirty seventh aspect of the invention, the positive polarity of the electric energy storage section is connected to the inductor through the first switch means, and from the opposite side terminal of the inductor, through the third switch means, is connected to the negative polarity of the electric energy storage section; the opposite side terminal of the inductor is connected to the output electrode to apply the electric pulse onto the patient through the second switch means and the inductor; and the output electrode is connected to the negative polarity of the electric energy storage section; to a portion between the first switch means and the inductor, two diodes are connected in series, in which the inductor side is the anode, and the first switch means side is the cathode; the capacitor and the resistor are inserted between a portion between the two diodes, and a portion between the inductor and the switch; the protective resistor is inserted between the output electrodes; and the apparatus has the charging circuit to charge the electric energy storage section; the two diodes are respectively inserted between both polarities of the electric energy storage section and the charging circuit; the voltage monitoring circuit is connected to both polarities of the electric energy storage section; the apparatus has the drive circuit to control the open/close operation of the first switch means, the drive circuit to control the open/close operation of the second switch means, and the drive circuit to control the open/close operation of the third switch means; and the three drive circuits and the charging circuit are structured so that these can be controlled by the microprocessor, thereby, the biphasic electric stimulation pulse waveform can be freely outputted, and the conventional problems are solved, and it is effective in terminating the fibrillation of the heart in the cardiac diseases.

In the electrotherapy apparatus according to the thirty eighth aspect of the invention, the positive polarity of the electric energy storage section is connected to the inductor through the first switch means, and from the opposite side terminal of the inductor, through the third switch means, is connected to the negative polarity of the electric energy storage section; the opposite side terminal of the inductor is connected to the output electrode to apply the electric pulse onto the patient through the second switch means and the inductor; and the output electrode is connected to the negative polarity of the electric energy storage section; to a portion between the first switch means and the inductor, the two diodes are connected in series, in which the inductor side is the anode, and the first switch means side is the cathode; the capacitor and the resistor are inserted between a portion between two diodes, and a portion between the inductor and the switch; the protective resistor is inserted between the output electrodes; and the apparatus has the charging circuit to charge the electric energy storage section; the two diodes are respectively inserted between both polarities of the electric energy storage section and the charging circuit; the voltage monitoring circuit is connected to both electrodes of the electric energy storage section; the apparatus has the drive circuit to control the open/close operation of the first switch means, the drive circuit to control the open/close operation of the second switch means, and the drive circuit to control the open/close operation of the third switch means; and the three drive circuits and the charging circuit are structured so that these can be controlled by the microprocessor; the current monitoring circuit is inserted between the positive polarity of the electric energy storage section and the first switch means; the resistor is inserted so that a portion between the current monitoring circuit and the first switch means, and a portion between the inductor and the second switch means are connected; the microprocessor at least has the ROM in which the data of the reference curve is previously stored, and the digital/analog conversion circuit to convert the data of the ROM to the analog data, the gain switching circuit, the pulse width modulation circuit in which at least the error amplifier is housed; the pulse width modulation circuit is connected so that the voltage signal from the digital/analog conversion circuit and the voltage signal from the gain switching circuit are inputted; the gain switching circuit is connected so that the control signal from the microprocessor, the signal from the current monitoring circuit, and the signal from the voltage monitoring circuit are inputted; thereby, the biphasic electric stimulation pulse waveform can be freely outputted, and the conventional problems are solved, and it is effective in terminating the fibrillation of the heart in the cardiac diseases.

The electrotherapy apparatus according to the thirty ninth aspect of the invention is the external type by which the stimulation pulse is applied onto the body surface of the patient, thereby, the same apparatus can be used for the other patient.

The electric energy delivering method of the electrotherapy apparatus according to the fortieth aspect of the invention is a method by which, the electric energy stored in the electric energy storage section is delivered to the patient in biphasic waveform, initially, the necessary electric energy is delivered in the first phase waveform, and next, the necessary electric energy, from the remained energy, is delivered in the second phase waveform within a predetermined time period, thereby, the second phase waveform having a predetermined electric energy can be applied to the patient within the optimum time period for the defibrillation, without depending on the impedance of the patient.

In the electric energy delivering method of the electrotherapy apparatus according to the forty first aspect of the invention, the electric energy stored in the electric energy storage section, is repeatedly delivered onto the patient in the first phase waveform and the second phase waveform at the plurality of times alternately (multiphasic output waveform), by freely forming the shape of the second phase waveform without depending on the impedance of the patient, there is a possibility that the more effective defibrillation can be conducted.

BRIEF DESCRIPTION OF DRAWINGS

FIG. 4 is a view explaining the current path when the first switch means is turned off at the time of the negative phase waveform output.

FIG. 5 is a block structural view showing the electrotherapy apparatus according to the second and third embodiments of the present invention.

DETAILED DESCRIPTION OF PREFERRED EMBODIMENTS

Figure 1:
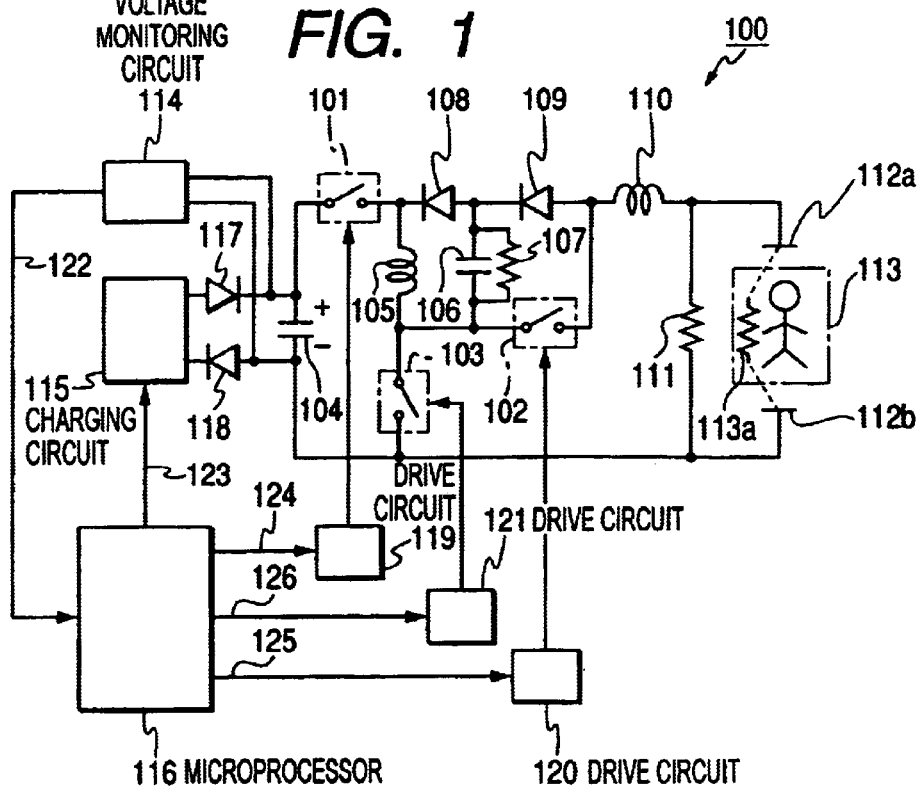
FIG. 1 is a block structural view showing an electrotherapy apparatus according to the first embodiment of the present invention.

Referring to the drawings, each embodiment of the electrotherapy apparatus of the present invention will be detailed below.

In each embodiment, the explanation is conducted as the first phase waveform is the positive phase, and the second phase waveform is the negative phase, however, it may be allowed that the first phase waveform is the negative phase, and the second phase waveform is the positive phase.

The First Embodiment

FIG. 1 is a block structural view showing the electrotherapy apparatus according to the first embodiment of the present invention.

As shown in FIG. 1, the electrotherapy apparatus 100 is structured as follows.

A positive polarity of the electric energy storage section 104 using a capacitor and the like, is connected to an inductor 105 through a switch 101 (the first switch means), and further, the opposite side terminal of the inductor 105 is connected to a negative polarity of the electric energy storage section 104 through a switch 103 (the third switch means). Further, the opposite side terminal of the inductor 105 is connected to the one output electrode 112a to apply an electric stimulation pulse onto the patient 113 (the impedance of the patient is 113a) through a switch 102 (the second switch means), through the inductor 110.

Further, the other output electrode 112b is connected to the negative polarity of the electric energy storage section 104.

A diode 108 and a diode 109 for reverse current prevention, whose inductor 110 side is the anode, and the switch 101 side is the cathode, are connected in series between the switch 101 and the inductor 110, and between two diodes, that is, between the cathode of the diode 109, and a portion between the inductor 105 and the switch 102, a capacitor 106 and a resistor 107 to smooth the waveform are inserted.

Further, a protective resistor 111 is inserted between the output electrodes 112a and 112b.

Charging to the electric energy storage section 104 is conducted by a charging circuit 115.

Incidentally, a diode 117 and a diode 118 for reverse current prevention are respectively inserted between both polarities of the electric energy storage section 104 and the charging circuit 115.

Further, a voltage monitoring circuit 114 is connected between both polarities of the electric energy storage section 104, and monitors the voltage stored in the electric energy storage section 104, and a voltage signal 122 to transmit the detected voltage is connected to a microprocessor 116.

Further, switches 101, 102, and 103 are connected so that the control of their open/close operations is conducted by a drive circuit 119 of the switch 101, drive circuit 120 of the switch 102, and drive circuit 121 of the switch 103, and these drive circuits 119, 120, and 121 are controlled by the control signals 124, 125, and 126 from a microprocessor 116. Further, the microprocessor 116 controls the charging circuit 115 by a control signal 123.

Incidentally, the switch 101 (the first switch means), switch 102 (the second switch means), and switch 103 (the third switch means) are preferably structured by semiconductor switches consisting of insulated gate bipolar transistors (IGBT).

An output control method of the electric stimulation pulse of the electrotherapy apparatus according to the first embodiment will be described bellow.

Initially, the charging operation of the electric energy to the electric energy storage section 104 will be described (step 1-1–1-7).

Step 1-1: A charge start command is inputted into the microprocessor 116.

Step 1-2: The microprocessor 116 outputs the control signals 124, 125, 126 to the drive circuits 119, 120, 121 of each switch so that the switches 101, 102, and 103 are in the continuous turning-off status.

Step 1-3: Switches 101, 102 and 103 are in the continuous turning-off status.

Step 1-4: The microprocessor 116 outputs the control signal 123 for the charging start to the charging circuit 115.

Step 1-5: The charging circuit 115 starts the energy charging to the electric energy storage section 104.

Step 1-6: The microprocessor 116 receives the voltage signal 122 from the voltage monitoring circuit 114, and when the voltage of the electric energy storage section 104 monitored by the voltage monitoring circuit 114 rises to a predetermined value, the microprocessor 116 outputs the control signal 123 for charging stop to the charging circuit 115.

Step 1-7: The charging circuit 115 stops the energy charging to the electric energy storage section 104.

Figure 2:
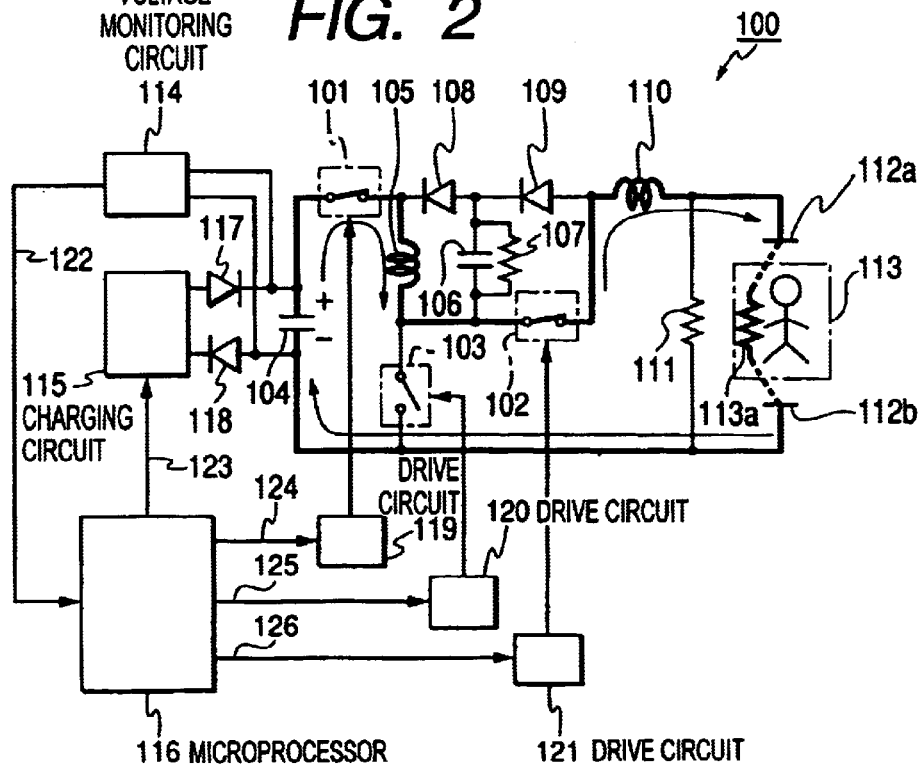
FIG. 2 is a view explaining a current path when a positive phase waveform is outputted.

Next, referring to FIG. 2, relating to the output operation of the electric energy to the output electrodes 112*a*, 112*b* to apply the electric stimulation pulse from the electric energy storage section 104 onto the patient, the operation at the time of the positive phase waveform output will be described (Step 1-8–Step 1-14). FIG. 2 is a view explaining the current path at the time of the positive phase waveform output.

Step 1-8: According to the pressing of the discharge start button (not shown) by the operator, the discharge start command is inputted into the microprocessor 116.

Step 1-9: The microprocessor 116 outputs control signals 124, 125 and 126 to the drive circuits 119, 120 and 121 so that the switch 101 and the switch 102 are in the continuous turning-on status, and the switch 103 is in the continuous turning-off status.

Step 1-10: The switch 101 and the switch 102 are in the continuous turning-on status, and the switch 103 is in the continuous turning-off status.

Step 1-11: The electric energy is delivered onto the patient 113 in the positive phase waveform. The voltage of the electric energy storage section 104 is decreased.

Step 1-12: For example, when the voltage of the electric energy storage section 104 is attenuated from the initial voltage to a predetermined rate (for example, 37%), according to the predetermined protocol, the microprocessor 116 outputs control signals 124, 125 and 126 to the drive circuits 119, 120 and 121 so that the switch 101 and the switch 102 are in the continuous turning-off status, and the switch 103 is in the continuous turning-on status.

Step 1-13: The switch 101 and the switch 102 are in the continuous turning-off status, and the switch 103 is in the continuous turning-on status.

Step 1-14: The electric energy output (positive phase waveform output) to the patient 113 is completed.

Next, relating to the output operation of the electric energy to the output electrodes 112*a* and 112*b* to apply the electric stimulation pulse onto the patient 113 from the electric energy storage section 104, the operation at the time of the negative phase waveform output will be explained by using FIG. 3(*a*), FIG. 4 and FIG. 3(*b*) (Step 1-15–Step 1-20).

Figure 3A:
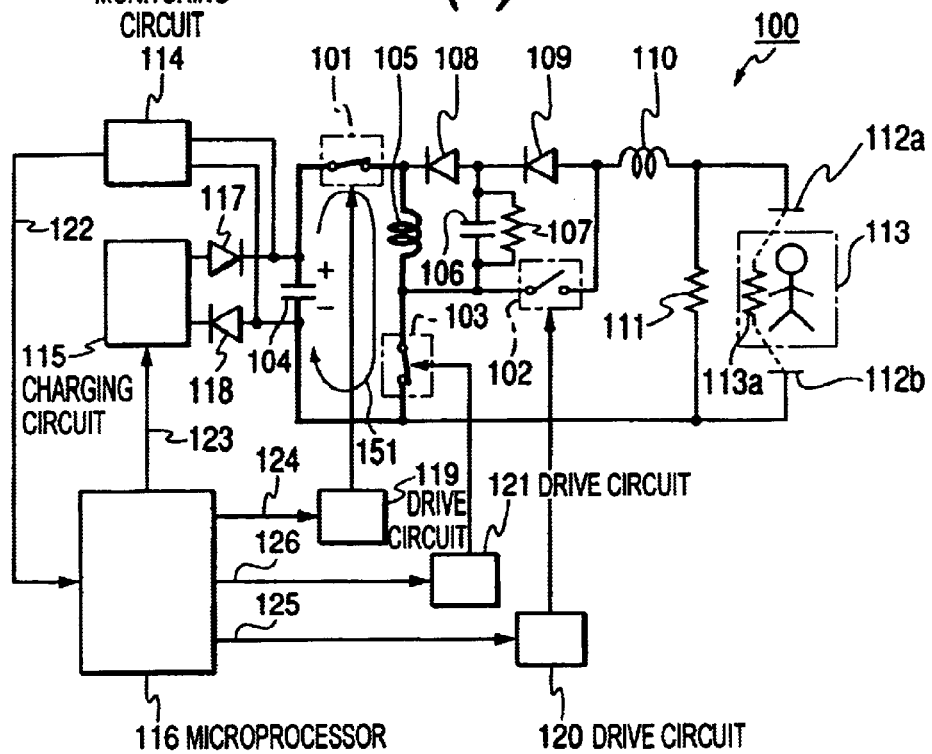
FIGS. 3(a) and (b) are views explaining the current path when the first switch means is turned on at the time of a negative phase waveform output.
Figure 3B:
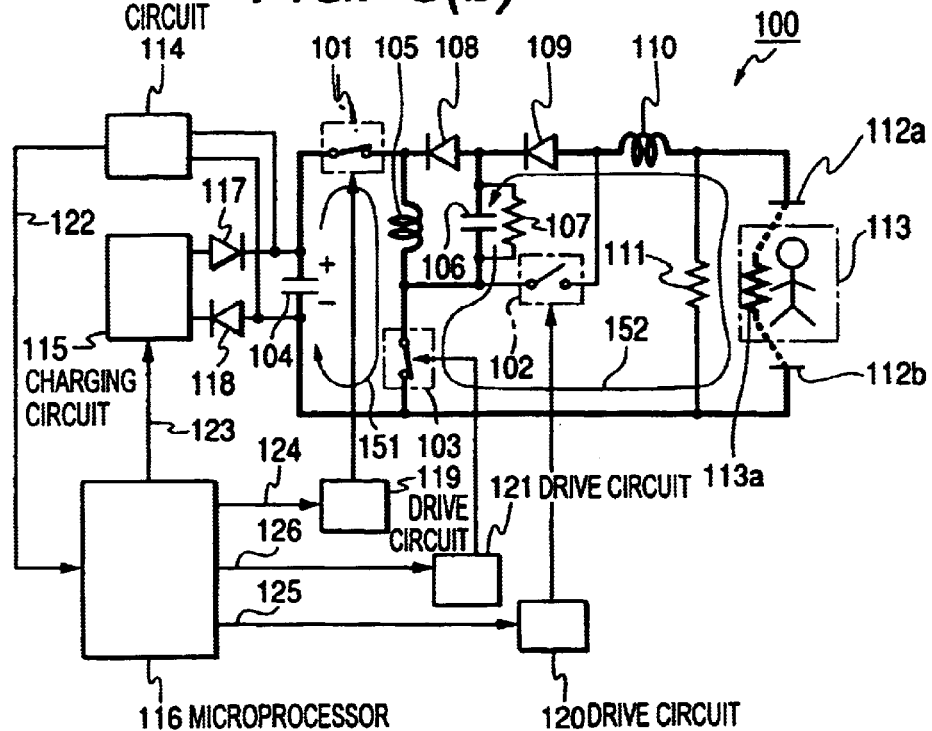

FIG. 3(*a*) is a view explaining the current path in the case of the turning-on status of the switch 101 for the first time at the time of the negative phase waveform output, FIG. 4 is a view explaining the current path in the case of the turning-off status of the switch 101 at the time of the negative phase waveform output, and FIG. 3(*b*) is a view explaining the current path in the case of the turning-on status of the switch 101 for the second and the subsequent time at the time of the negative phase waveform output.

As shown in FIG. 3(*a*), when the switch 101 (the first switch means) is in the turning-on status for the first time at the time of the negative phase waveform output, the current flows along the current path 151 shown by an arrow. Then, the inductor 105 and the capacitor 104 forms the closed circuit in the apparatus without including the patient.

At this time, when the current flows though the current path 151, the electric energy in the electric energy storage section 104 is stored in the inductor 105 as the magnetic energy.

In this stage, the electric energy is not outputted to the patient 113.

As shown in FIG. 4, when the switch 101 (the first switch means) is in the turning-off status at the time of the negative phase waveform output, the current flows along the current path 153 shown by an arrow.

In this case, the diodes 108 and 109 are in the turning-on status, and the magnetic energy stored in the inductor 105 is outputted as the electric energy, and the current flows along the current path 153.

Accordingly, the electric energy is delivered to the patient 113.

Further, simultaneously the current flows into the capacitor 106, and the electric energy is stored in the capacitor 106.

As shown in FIG. 3(*b*), when the switch 101 (the first switch means) is in the turning-on status for the second and the subsequent time at the time of the negative phase waveform output, the current flows along the arrowed current paths 151 and 152.

In this case, the diode 108 is in the turning-off status, and the diode 109 maintains the turning-on status.

Accordingly, the electric energy stored in the capacitor 106 is outputted, and the current flows along the current path 152.

Accordingly, the status in which the electric energy is delivered to the patient 113, is maintained.

Further, simultaneously, when the current flows through the current path 151, the electric energy in the electric energy storage section 104 is stored in the inductor 105 as the magnetic energy. The operation at the time of the negative phase waveform output will be explained as follows:

Step 1-15: The microprocessor 116 outputs the control signal to control the turning-on/off of the switch 101 to the drive circuit 119 of the switch 101 so that the desired output waveform can be outputted, by using a previously set reference curve, that will be explained later.

Step 1-16: The switch 101 conducts the switching operation which repeats the turning-on/off. In the steps herein, by the switching operation which repeats the turning-on/off of the switch 101, the conditions of the current paths follow from FIG. 3(*a*), FIG. 4, to FIG. 3(*b*), and after that, the conditions of FIG. 4 and FIG. 3(*b*) are repeated.

Step 1-17: The electric energy is delivered to the patient 113 in the negative phase waveform. The voltage in the electric energy storage section 104 is decreased via the inductor 106 and the capacitor 107.

Step 1-18: According to the predetermined protocol, in order to end the energy output to the patient in the negative phase waveform, the microprocessor 116 outputs the control signal 124 to the drive circuit 119 so that the switch 101 is in the continuous turning-off status.

Step 1-19: The switch 101 is in the continuous turning-off status.

Step 1-20: The energy output (negative phase waveform output) to the patient 113 is completed.

The Second Embodiment

FIG. 5 is a block structural view showing the electrotherapy apparatus according to the second embodiment of the present invention.

As shown in FIG. 5, this electrotherapy apparatus 130 is structured as follows. Portions common to each portion in the above described FIG. 1 are shown by the same numeral codes, and the explanation is neglected.

In the electrotherapy apparatus according to the second embodiment, the following structures are added to the electrotherapy apparatus according to the first embodiment.

A current monitoring circuit 131 is inserted between the positive polarity of the electric energy storage section 104 and the switch 101, and further, a resistor 132 is inserted in such a manner that a portion between the current monitoring circuit 131 and the switch 101, is connected to a portion between the inductor 105 and the switch 102.

Further, the microprocessor 116 has at least a ROM 141 in which the data of the reference curve is previously stored, and a digital/analog conversion circuit 140 to convert the ROM data into the analog data.

Further, a gain switching circuit 133, and a pulse width modulation circuit 143 in which the error amplifier 142 is housed are provided, and the pulse width modulation circuit 143 is connected so that the voltage signal 138 (the voltage of the reference curve) from the digital/analog conversion circuit 140, and the voltage signal 137 from the gain switching circuit 133 are inputted.

Further, the gain switching circuit 133 is connected so that the control signal 136 from the microprocessor 116, the signal 135 from the current monitoring circuit 131, and the signal 134 from the voltage monitoring circuit 114 are inputted.

The electric energy delivering method of the electrotherapy apparatus according to the present embodiment will be detailed below.

This method is an electric energy delivering method to output control so that the voltage which is lowered corresponding to the energy amount outputted from the electric energy storage section 104 is decreased corresponding to a function of the predetermined time and voltage (Step 2-1–Step 2-15).

Step 2-1: The charging to the electric energy storage section 104 is completed. At this time, switches 101, 102, and 103 are in the turning-off status.

Step 2-2: According to the pressing of the discharge start button (not shown) by the operator, the discharge start command is inputted into the microprocessor 116.

Step 2-3: The microprocessor 116 calculates the discharging end voltage (V1t) of the first phase (positive phase) and the discharging end voltage (V2t) of the second phase (negative phase) from the voltage of the electric energy storage section 104 at this time.

Step 2-4: The microprocessor 116 outputs the control signal 136 for the gain switching to the gain switching circuit 133 according to the calculated value of V1t.

Step 2-5: The microprocessor 116 outputs control signals 124, 125 and 126 to each of drive circuits 119, 120 and 121 so that the switch 101 and switch 102 are in the continuous turning-on status, and the switch 103 is in the continuous turning-off status.

Step 2-6: The switch 101 and switch 102 are in the continuous turning-on status, and the switch 103 is in the continuous turning-off status.

Step 2-7: The electric energy is delivered to the patient in the positive phase waveform. The voltage of the electric energy storage section 104 is decreased.

Step 2-8: When the voltage of the electric energy storage section 104 is decreased to the V1t, the microprocessor 116 outputs control signals 124, 125 and 126 to each of drive circuits 119, 120 and 121 so that the switch 101 and switch 102 are in the continuous turning-off status, and the switch 103 is in the continuous turning-on status.

Step 2-9: The switch 101 and switch 102 are in the continuous turning-off status, and the switch 103 is in the continuous turning-on status.

Step 2-10: The microprocessor 116 outputs the voltage signal 138 of the discharge voltage reference curve which is previously stored in the ROM 141.

Step 2-11: The error amplifier 142 of the pulse width modulation circuit 143 compares the voltage signal 138 of the reference curve to the voltage signal 137 of the electric energy storage section 104, and outputs the signal 139 to control the rate of the on (turning-on)-time of the switch 101 so that the voltage of the electric energy storage section 104 is equal to the reference curve to the drive circuit 119 of the switch 101.

Step 2-12: The switch 101 conducts the switching operation at the rate of the on (turning-on) time determined in Step 2-11.

Step 2-13: The energy is delivered to the patient 113 in the negative phase waveform. The voltage of the electric energy storage section 104 is decreased.

Step 2-14: When the voltage of the electric energy storage section 104 is lowered to the second phase (negative phase) end voltage V2t, the microprocessor 116 outputs the control signal 124 to the drive circuit 119 of the switch 101 so that the switch 101 is in the continuous turning-off status.

Step 2-15: The energy output to the patient 113 is completed.

The Third Embodiment

In the electrotherapy apparatus according to the present embodiment, the structure is the same as the second embodiment shown in FIG. 5, and only the electric energy delivering method is different, and the method is detailed below.

This electric energy delivering method is a method which output controls so that the current which is increased corresponding to the energy amount outputted from the electric energy storage section 104, is increased corresponding to the function of the predetermined time and current (Step 3-1–Step 3-15). Here, the current which flows from the electric energy accumulation section 14 is converted into the corresponding voltage by the current monitoring circuit 131. For this reason, the function of the predetermined time and current is previously converted into the function of time and voltage corresponding to the current. The converted function is used as the discharge current reference curve.

Step 3-1: Charging to the electric energy storage section 104 is completed. At this time, switches 101, 102 and 103 are in the turning-off status.

Step 3-2: By the pressing of the discharge start button(not shown) by the operator, the discharge start command is inputted into the micro processor 116.

Step 3-3: The microprocessor 116 calculates the discharging end voltage V1t of the first phase (positive phase) and the discharging end voltage V2t of the second phase (negative phase) from the voltage of the electric energy storage section 104 at this time.

Step 3-4: The microprocessor 116 outputs the control signal 136 for the gain switching to the gain switching circuit 133 according to the calculated value of V1t.

Step 3-5: The microprocessor 116 outputs control signals 124, 125 and 126 to each of drive circuits 119, 120 and 121 so that the switch 101 and switch 102 are in the continuous turning-on status, and the switch 103 is in the continuous turning-off status.

Step 3-6: The switch 101 and switch 102 are in the continuous turning-on status, and the switch 103 is in the continuous turning-off status.

Step 3-7: The electric energy is delivered to the patient 113 in the positive phase waveform. The voltage of the electric energy storage section 104 is decreased.

Step 3-8: When the voltage of the electric energy storage section 104 is decreased to the V1t, the microprocessor 116 outputs control signals 124, 125 and 126 to each of drive circuits 119, 120 and 121 so that the switch 101 and switch 102 are in the continuous turning-off status, and the switch 103 is in the continuous turning-on status.

Step 3-9: The switch 101 and switch 102 are in the continuous turning-off status, and the switch 103 is in the continuous turning-on status.

Step 3-10: The microprocessor 116 outputs the voltage of the discharge current reference curve which is previously stored in the ROM 141.

Step 3-11: The error amplifier 142 of the pulse width modulation circuit 143 compares the voltage of the current reference curve to the voltage converted from the current which flows from the electric energy storage section 104 by the current monitoring circuit 131, and outputs the signal 139 to control the rate of the on (turning-on)-time of the switch 101 so that the both voltages are equal, to the drive circuit 119 of the switch 101.

Step 3-12: The switch 101 conducts the switching operation at the rate of the on (turning-on)-time determined in Step 3-11.

Step 3-13: The energy is delivered to the patient 113 in the negative phase waveform. The voltage of the electric energy storage section 104 is decreased.

Step 3-14: When the voltage of the electric energy storage section 104 is lowered to the second phase (negative phase) end voltage V2t, the microprocessor 116 outputs the control signal to the drive circuit 119 of the switch 101 so that the switch 101 is in the continuous turning-off status.

Step 3-15: The energy output to the patient 113 is completed.

Examples of the output waveform of the electrotherapy apparatus in the first to third embodiments are shown in FIG. 6(a) to (d).

The Common Structure of Fourth to Sixth Embodiments

Figure 7:
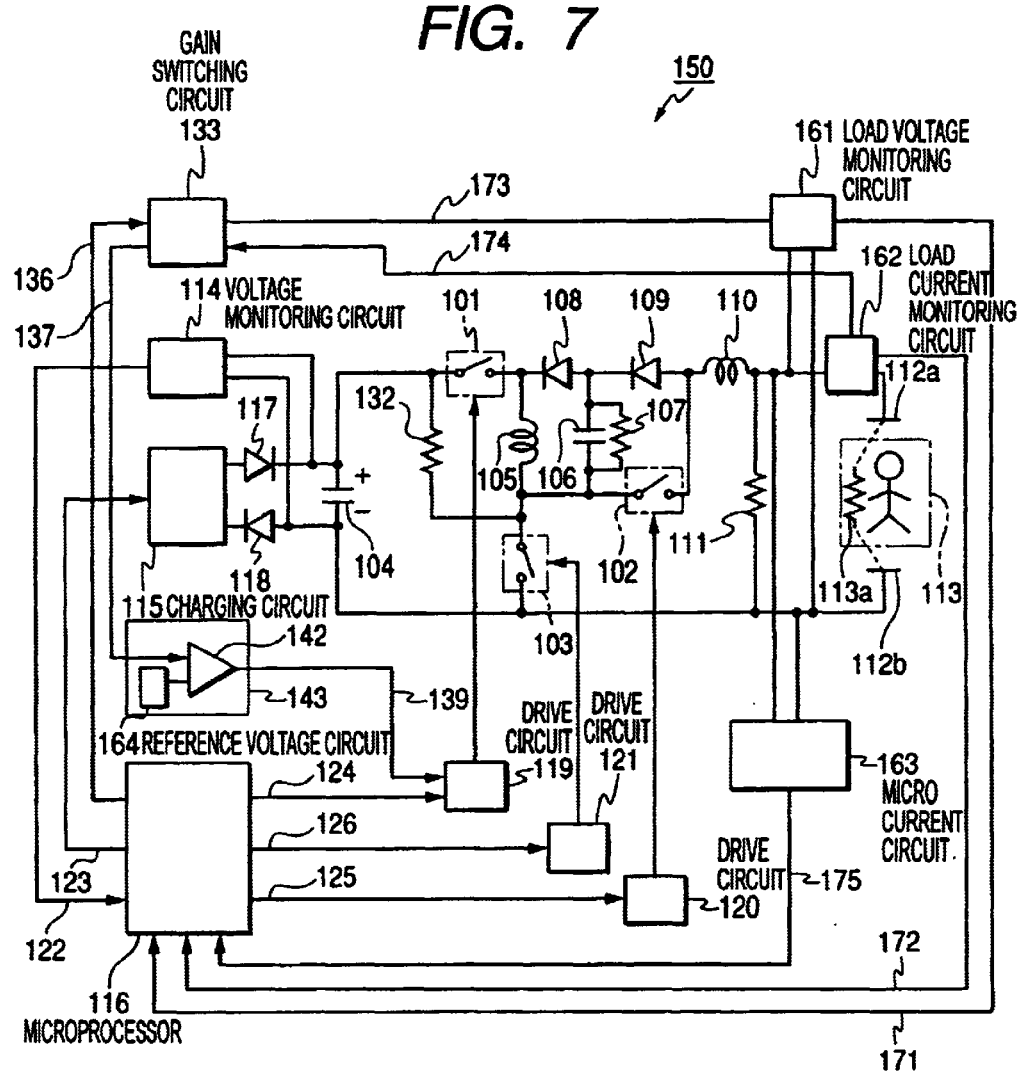
FIG. 7 is a block structural view showing the electrotherapy apparatus according to the fourth to sixth embodiments of the present invention.

FIG. 7 is a block structural view showing the electrotherapy apparatus 150 according to the fourth to sixth embodiments of the present invention. As shown in FIG. 7, in the electrotherapy apparatus 150, a load voltage monitoring circuit 161, load current monitoring circuit 162, and further, the reference voltage generating circuit 164 in the pulse width modulation circuit 143 are added to the electrotherapy apparatus according to the second embodiment.

The common part to that of FIG. 1 to 5 is shown by the same numeral code, and its explanation is omitted.

Figure 8:
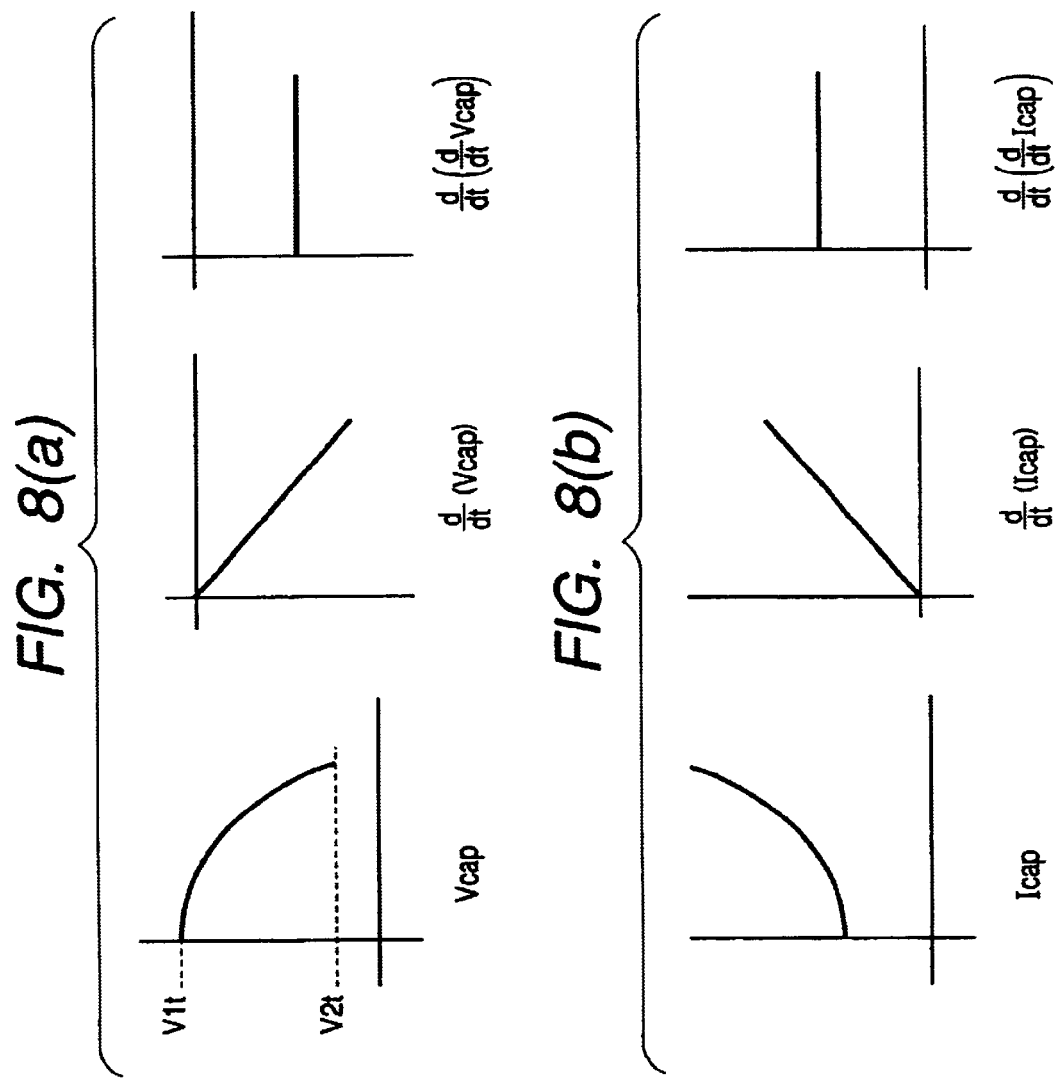
FIGS. 8(a) and (b) are views showing an example of the preferable reference curves of the voltage and current according to the fourth to sixth embodiments of the present invention.
Figure 9:
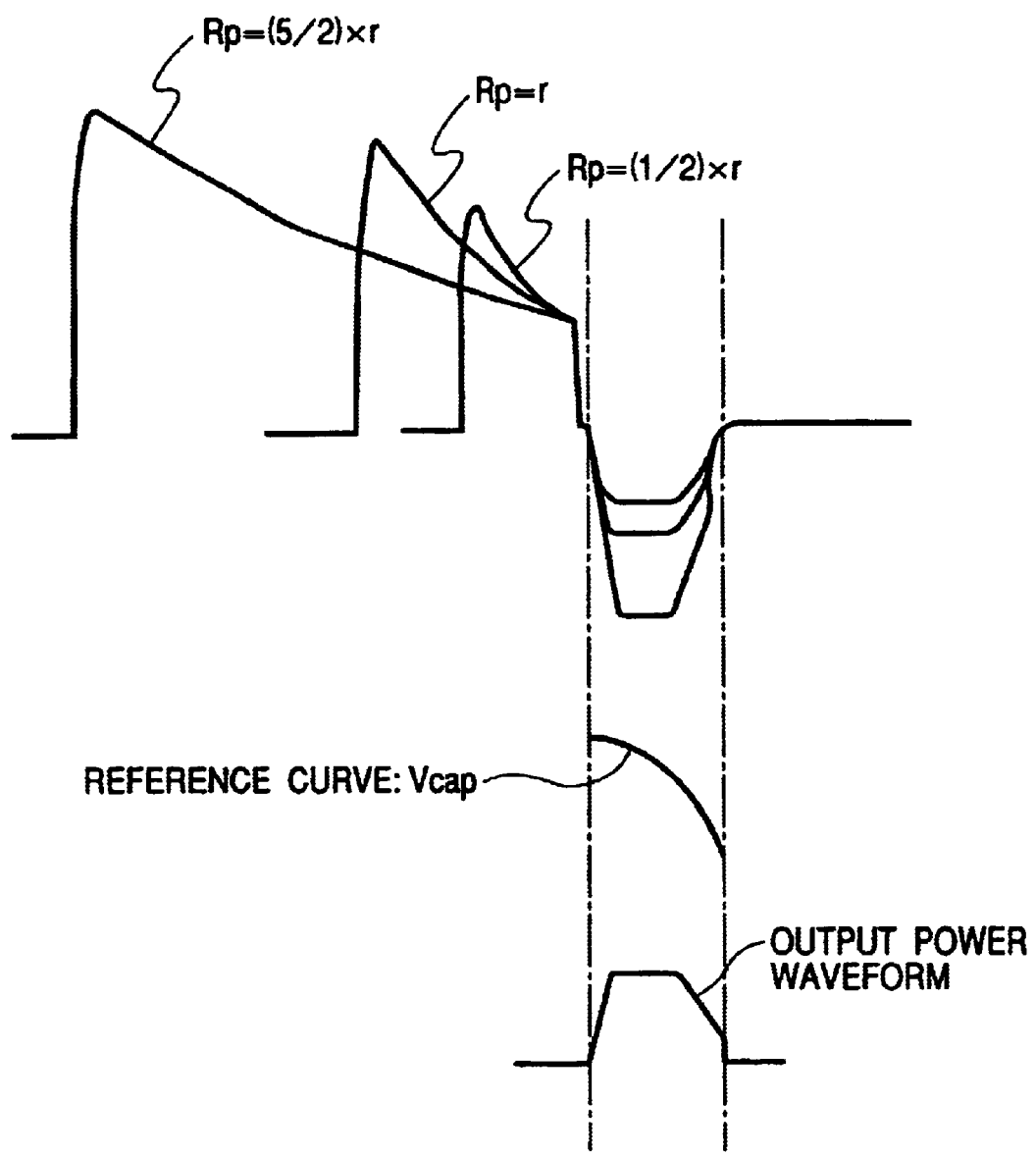
FIG. 9 is a view showing an example of the relationship between the impedance of the patient and the output voltage waveform according to the fourth to sixth embodiments of the present invention.
Figure 10A:
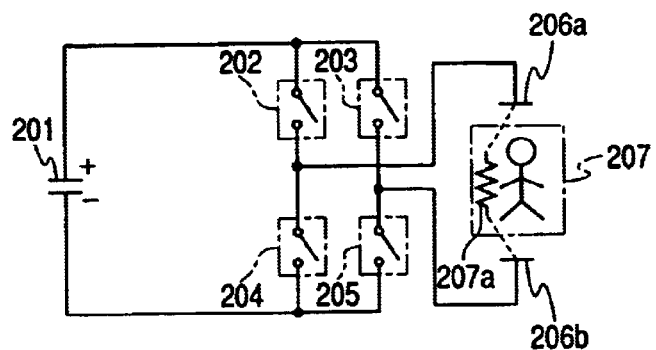
FIGS. 10(a) and (b) are views for explaining the output circuit of the conventional biphasic defibrillator.
Figure 10B:
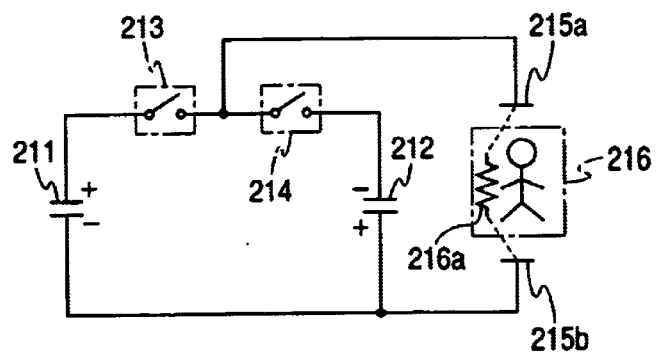
Figure 11A:
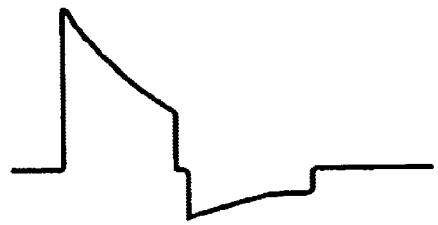
FIGS. 11(a) and (b) are views for explaining the output waveforms of the conventional biphasic defibrillator.
Figure 11B:
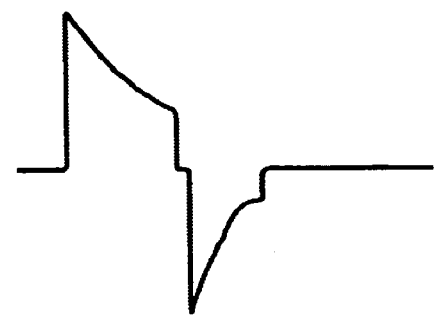

Further, FIG. 8 is a view showing examples of the preferable reference curves of the voltage of the electric energy storage section 104 and the current which flows from the electric energy storage 104 (In case of current reference curve, the current is converted into voltage by the current monitoring circuit). FIG. 9 is a view showing an example of the relationship of the impedance of the patient and the output voltage waveform.

As shown in FIG. 8, as the reference curve, it is preferable to use the voltage value Vcap, voltage differential value d/dt (Vcap), voltage double differential value d/dt (d/dt Vcap), current value Icap, current differential value d/dt (Icap), and current double differential value d/dt (d/dt Icap).

In FIG. 9, Rp is the impedance of the patient, and the output voltage waveforms (the first phase and the second phase) in the case of the standard impedance r, smaller impedance (1/2) r, and larger impedance (5/2) r, are shown.

As shown in FIG. 9, the larger the impedance of the patient is, the longer is the duration of the truncated exponential waveform of the first phase.

Further, when the electric power of the second phase waveform is controlled according to the reference curve of the voltage value Vcap, the necessary energy can be supplied in a predetermined time period, without depending on the impedance of the patient. That is, as shown in the view, because the larger the impedance of the patient is, the higher the amplitude of the outputted output voltage is, the output electric power waveform becomes constant without depending on Rp.

The Fourth Embodiment

The electrotherapy apparatus according to the present embodiment has a patient parameter measuring means for measuring the patient parameter, and an output electrode parameter measuring means (the load voltage monitoring circuit 161, load current monitoring circuit 162) for measuring the voltage generated between output electrodes or the current flowing to the output electrode.

The electrotherapy apparatus has a control means for controlling so that the electric power of the electric energy becomes constant without depending on the value of the patient parameter, according to the patient parameter measured by the patient parameter measuring means before the second phase waveform is outputted, and to the value relating to the voltage between the output electrodes, or the value relating to the current flowing to the output electrode, measured by the output electrode parameter measuring means during the output of the second phase waveform.

That is, the present embodiment uses the patient impedance measured before the second phase (negative phase) output and the patient voltage (or current) during the second phase (negative phase) output.

The present embodiment is used in the case where, as the patient parameter measuring means, the patient impedance is calculated from the change of the output signal 122 form the voltage monitoring circuit 114 during the first phase output.

Referring to FIG. 7 to FIG. 9, the patient parameter measuring method and the electric energy delivering method to the patient by the electrotherapy apparatus according to the present embodiment, will be detailed below.

Step 4-1: Charging to the electric energy storage section 104 is completed. At this time, switches 101, 102 and 103 are in the turning-off status.

Step 4-2: By the pressing of the discharge start button(not shown) by the operator, the discharge start command is inputted into the micro processor 116.

Step 4-3: The microprocessor 116 calculates the discharging end voltage V1t of the first phase (positive phase) and the discharging end voltage V2t of the second phase (negative phase) from the voltage of the electric energy storage section 104 at this time.

Step 4-5: The microprocessor 116 outputs control signals 124, 125 and 126 to each of switch drive circuits 119, 120 and 121 so that the switch 101 and switch 102 are in the continuous turning-on status, and the switch 103 is in the continuous turning-off status.

Step 4-6: The switch 101 and switch 102 are in the continuous turning-on status, and the switch 103 is in the continuous turning-off status.

Step 4-7: The electric energy is delivered to the patient 113 in the positive phase waveform. The voltage of the electric energy storage section 104 is decreased. The output signal 122 from the voltage monitoring circuit 114 during the first phase waveform output is inputted to the microprocessor 116, and from the rate of its time change, the microprocessor 116 calculates the impedance of the patient 113 (corresponding to the patient parameter measurement).

Step 4-8: When the voltage of the electric energy storage section 104 is decreased to the V1t, the microprocessor 116 outputs control signals 124, 125 and 126 to each of drive circuits 119, 120 and 121 so that the switch 101 and switch 102 are in the continuous turning-off status, and the switch 103 is in the continuous turning-on status.

Step 4-9: The switch 101 and switch 102 are in the continuous turning-off status, and the switch 103 is in the continuous turning-on status.

The microprocessor 116 outputs the gain switching signal 136 determined by the calculated patient impedance and the voltage of the electric energy storage section 104 at the time of the output start of the first phase (positive phase), which is monitored by the voltage monitoring circuit 114 and outputted, to the gain switching circuit 133.

Step 4-11: The error amplifier 142 of the pulse width modulation circuit 143 compares the output signal 137 of the gain switching circuit 133 by the gain switched output signal 173 of the load voltage monitoring circuit 161 of the patient (corresponding to the value relating to the voltage between the output electrodes), or the gain switched output signal 174 of the load current monitoring circuit 162 of the patient (corresponding to the value relating to the current flowing to the output electrode)to the constant output voltage from the reference voltage generation circuit 164, and outputs the signal 139 to control the rate of the on (turning-on)-time of the switch 101 so that the voltage of the output signal 137 of the gain switching circuit 133 is equal to the constant output voltage from the reference voltage generation circuit 164, to the drive circuit 119 of the switch 101.

Step 4-12: The switch 101 conducts the switching operation at the rate of the on (turning-on)-time determined in Step 4-11.

Step 4-13: The energy is delivered to the patient 113 in the negative phase waveform. The voltage of the electric energy storage section 104 is decreased.

Step 4-14: When the voltage of the electric energy storage section 104 is lowered to the second phase (negative phase) discharging end voltage V2t, the microprocessor 116 outputs the control signal 124 to the drive circuit 119 of the switch 101 so that the switch 101 is in the continuous turning-off status.

Step 4-15: The energy output to the patient 113 is completed.

In the present embodiment, the constant output voltage from the reference voltage generation circuit 164 is always constant, without depending on the impedance of the patient 113, and the large and small value of the energy supplied to the patient 113.

The Fifth Embodiment

The electrotherapy apparatus according to the present embodiment has the patient parameter measuring means for measuring the patient parameter, and the output electrode parameter measuring means (load voltage monitoring circuit 161, load current monitoring circuit 162) for measuring the voltage generated between the output electrodes or the current flowing to the output electrode.

The control means of the present embodiment controls so that the electric power of the electric energy becomes constant without depending on the value of the patient parameter, according to the patient parameter measured by the patient parameter measuring means before the second phase waveform is outputted, and to the value relating to the voltage between output electrodes or the value relating to the current flowing to the output electrode, measured by the output electrode parameter measuring means during the output of the second phase waveform.

That is, this control means is a control method by which the impedance of the patient measured before the output of the second phase (negative phase) and the voltage (or current) of the patient during the output of the second phase (negative phase), are used, and the patient parameter measuring means is used in the case where the impedance of the patient is calculated by using the high frequency micro current.

Referring to FIG. 7 to FIG. 9, the patient parameter measuring method and the electric energy delivering method to the patient by the electrotherapy apparatus according to the present embodiment, will be detailed below.

Step 5-1: Charging to the electric energy storage section 104 is completed. At this time, switches 101, 102 and 103 are in the turning-off status. The high frequency micro current circuit 163 supplies the high frequency micro current to the patient 113 through the electrodes 112a and 112b, and the feedback signal from the patient 113 to the supplied high frequency micro current is detected and processed, and the processed signal 175 is outputted to the microprocessor 116.

Step 5-2: According to the pressing of the discharge start button (not shown) by the operator, the discharge start command is inputted into the micro processor 116. The microprocessor 116 calculates the impedance of the patient from the output signal 175 from high frequency micro current circuit 163 (corresponding to the patient parameter measuring means).

Step 5-3: The microprocessor 116 calculates the discharging end voltage V1t of the first phase (positive phase) and the discharging end voltage V2t of the second phase (negative phase) from the voltage of the electric energy storage section 104 at this time.

Step 5-5: The microprocessor 116 outputs control signals 124, 125 and 126 to each of the switch drive circuits 119, 120 and 121 so that the switch 101 and switch 102 are in the continuous turning-on status, and the switch 103 is in the continuous turning-off status.

Step 5-6: The switch 101 and switch 102 are in the continuous turning-on status, and the switch 103 is in the continuous turning-off status.

Step 5-7: The electric energy is delivered to the patient 113 in the positive phase waveform. The voltage of the electric energy storage section 104 is decreased.

Step 5-8: When the voltage of the electric energy storage section 104 is decreased to the V1t, the microprocessor 116 outputs control signals 124, 125 and 126 to each of the switch drive circuits 119, 120 and 121 so that the switch 101 and switch 102 are in the continuous turning-off status, and the switch 103 is in the continuous turning-on status.

Step 5-9: The switch 101 and switch 102 are in the continuous turning-off status, and the switch 103 is in the continuous turning-on status.

The microprocessor 116 outputs the gain switching signal 136, determined by the calculated impedance of the patient 113 and the voltage of the electric energy storage section 104 at the time of the output start of the first phase, which is monitored and outputted by the voltage monitoring circuit 114, to the gain switching circuit 133.

Step 5-11: The error amplifier 142 of the pulse width modulation circuit 143 compares the output signal 137 of the gain switching circuit 133 by the gain switched output signal 173 of the load voltage monitoring circuit 161 of the patient (corresponding to the value relating to the voltage between electrode), or the gain switched output signal 174 of the load current monitoring circuit 162 of the patient (corresponding to the value relating to the current flowing to the output electrode), to the constant output voltage from the reference voltage generation circuit 164, and outputs the signal 139 to control the rate of the on (turning-on)-time of the switch 101 so that the voltage of the output signal 137 of the gain switching circuit 133 is equal to the constant output voltage from the reference voltage generation circuit 164, to the drive circuit 119 of the switch 101.

Step 5-12: The switch 101 conducts the switching operation at the rate of the on (turning-on)-time determined in Step 5-11.

Step 5-13: The energy is delivered to the patient 113 in the negative phase waveform. The voltage of the electric energy storage section 104 is decreased.

Step 5-14: When the voltage of the electric energy storage section 104 is lowered to the second phase (negative phase) discharging end voltage V2t, the microprocessor 116 outputs the control signal 124 to the drive circuit 119 of the switch 101 so that the switch 101 is in the continuous turning-off status.

Step 5-15: The energy output to the patient 113 is completed.

The Sixth Embodiment

The electrotherapy apparatus according to the present embodiment has the patient parameter measuring means for measuring the patient parameter, and the output electrode parameter measuring means (load voltage monitoring circuit 161, load current monitoring circuit 162) for measuring the voltage generated between the output electrodes or the current flowing to the output electrode.

The control means of the present embodiment controls the switching operation of the switch, according to the patient parameter measured by the patient parameter measuring means before the second phase waveform is outputted, and to the value relating to the voltage between output electrodes or the value relating to the current flowing to the output electrode, measured by the output electrode parameter measuring means during the output of the second phase waveform.

That is, this control method is a control method by which the impedance of the patient measured before the output of the second phase (negative phase) and the voltage (or current) of the patient during the output of the second phase (negative phase), are used, and the patient parameter measuring means is used in the case where the impedance of the patient is calculated by using the patient voltage and the patient current.

Referring to FIG. 7 to FIG. 9, the patient parameter measuring method and the electric energy delivering method to the patient by the electrotherapy apparatus according to the present embodiment, will be detailed below.

Step 6-1: Charging to the electric energy storage section 104 is completed. At this time, switches 101, 102 and 103 are in the turning-off status.

Step 6-2: According to the pressing of the discharge start button (not shown) by the operator, the discharge start command is inputted into the micro processor 116.

Step 6-3: The microprocessor 116 calculates the discharging end voltage (V1t) of the first phase (positive phase) and the discharging end voltage (V2t) of the second phase (negative phase) from the voltage of the electric energy storage section 104 at this time.

Step 6-5: The microprocessor 116 outputs control signals 124, 125 and 126 to each of the switch drive circuits 119, 120 and 121 so that the switch 101 and switch 102 are in the continuous turning-on status, and the switch 103 is in the continuous turning-off status.

Step 6-6: The switch 101 and switch 102 are in the continuous turning-on status, and the switch 103 is in the continuous turning-off status.

Step 6-7: The electric energy is delivered to the patient in the positive phase waveform. The voltage of the electric energy storage section 104 is decreased.

The output signal 171 from the load voltage monitoring circuit 161 of the patient during the output of the first phase, and the output signal 172 from the load current monitoring circuit 162 of the patient are inputted into the microprocessor 116, and the microprocessor 116 calculates the impedance of the patient 113 by using these signals (corresponding to the measurement of the patient parameter).

Step 6-8: When the voltage of the electric energy storage section 104 is decreased to the V1t, the microprocessor 116 outputs control signals 124, 125 and 126 to each of the switch drive circuits 119, 120 and 121 so that the switch 101 and switch 102 are in the continuous turning-off status, and the switch 103 is in the continuous turning-on status.

Step 6-9: The switch 101 and switch 102 are in the continuous turning-off status, and the switch 103 is in the continuous turning-on status.

The microprocessor 116 outputs the gain switching signal 136, determined by the calculated impedance of the patient and the voltage of the electric energy storage section 104 at the time of the output start of the first phase, which is monitored and outputted by the voltage monitoring circuit 114, to the gain switching circuit 133.

Step 6-10: The error amplifier 142 of the pulse width modulation circuit 143 compares the output signal 173 of the gain switched load voltage monitoring circuit 161 of the patient (corresponding to the value relating to the voltage between the output electrodes), or the output signal 137 of the gain switching circuit 133 by the gain switched load current monitoring circuit 162 of the patient (corresponding to the value relating to the current flowing to the output electrode), to the constant output voltage from the reference voltage generation circuit 164, and outputs the signal 139 to control the rate of the on (turning-on)-time of the switch 101 so that the voltage of the output signal 137 of the gain switching circuit 133 is equal to the constant output voltage from the reference voltage generation circuit 164, to the drive circuit 119 of the switch 101.

Step 6-11: The switch 101 conducts the switching operation at the rate of the on (turning-on)-time determined in Step 2-11.

Step 6-12: The energy is delivered to the patient 113 in the negative phase waveform. The voltage of the electric energy storage section 104 is decreased.

Step 6-13: When the voltage of the electric energy storage section 104 is lowered to the second phase (negative phase) discharging end voltage V2t, the microprocessor 116 outputs the control signal 124 to the drive circuit 119 of the switch 101 so that the switch 101 is in the continuous turning-off status.

6-14: The energy output to the patient 113 is completed.

In the present embodiment, the same reference curve as in the other embodiments is not used. Alternatively, the reference voltage which is independent of the impedance of the patient or the delivering energy, is used.

Further, according to the impedance of the patient and the delivering energy, the gain of the comparative object (the voltage of the patient or the current of the patient) of the reference voltage is set.

Figure 6A:
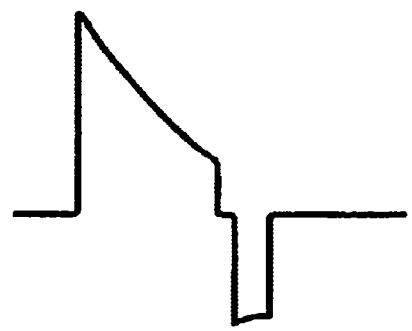
FIGS. 6(a) to (d) are views for explaining an output waveform of the electrotherapy apparatus according to the first to third embodiments of the present invention.
Figure 6B:
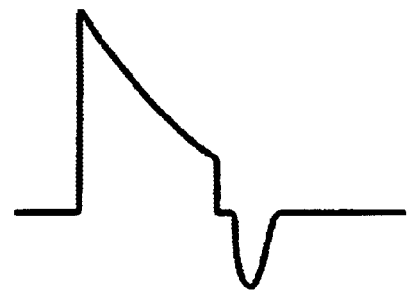
Figure 6C:
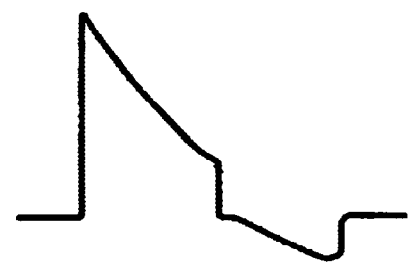
Figure 6D:
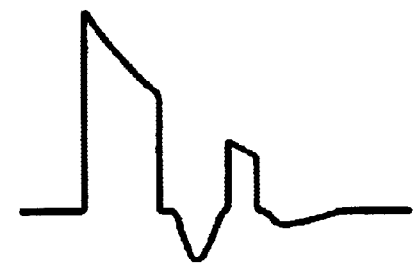

Incidentally, in each of the first to sixth embodiment, when the electric energy stored in the electric energy storage section 104 is delivered onto the patient 113 in the first phase (positive phase) waveform and the second phase (negative phase) waveform, initially, the necessary electric energy is delivered in the first phase (positive phase) waveform, next, from the remained energy, the necessary electric energy can be delivered in the second phase (negative phase) waveform for a predetermined time period, and further, the multiphasic waveform by which the electric energy stored in the electric energy storage section is delivered onto the patient 113 in the first phase (positive phase) waveform and the second phase (negative phase) waveform by alternately repeating them a plurality of times, can be easily realized (the waveform in FIG. 6(d)).

Further, in the above-described embodiments, in the first phase, the truncated exponential waveform, and in the second phase, the electric power control waveform according to the reference curve are outputted, however, alternatively, in the first phase, initially, the electric power control waveform, and next, in the second phase, the truncated exponential waveform may be outputted.

When the multiphasic waveform is outputted, it can be appropriately selected whether, in the third phase and the subsequent, the truncated exponential waveform is outputted, or the electric power control waveform is outputted.

Further, the stimulation pulse applied onto the patient, described in the above embodiments, is appropriate for terminating the fibrillation of the heart in cardiac disease, however, to the other medical treatments in which the high voltage electric stimulation pulse is required, the electrotherapy apparatus of the present invention can be applied.

As detailed above, according to the first aspect of the invention, the apparatus has the electric energy storage section to generate the stimulation pulse, and the output electrode to apply the stimulation pulse to the patient, and it structured in such a manner that the polarity of the voltage outputted to the output electrode is reversed, and is structured such that at least the first phase waveform and the second phase waveform of the electric energy are outputted from the output electrode, and the shape of the second phase waveform of the electric energy can be controlled, thereby, the output waveform of the second phase (negative phase) can be freely set without depending on the voltage (V1t) of the electric energy storage section at the time of the start of the second phase (negative phase). That is, the second phase (negative phase) output voltage (the hither voltage than V1t can be outputted), output current, and output electric power can be freely set, and further, the electrotherapy apparatus by which the necessary energy can be delivered within an arbitrary time period, can be provided.

According to the electrotherapy apparatus of the second aspect of the invention, the apparatus has the electric energy storage section to generate the stimulation pulse, and the output electrode to apply the stimulation pulse to the patient, and it structured in such a manner that the polarity of the voltage outputted to the output electrode is reversed, and is structured such that at least the first phase waveform and the second phase waveform of the electric energy are outputted from the output electrode, and by the outputted second phase waveform of the electric energy, the necessary electric energy is delivered within a predetermined time period, thereby, the predetermined second phase (negative phase) waveform of the electric energy can be delivered to the patient within an optimum time period for the defibrillation without depending on the impedance of the patient, and the electrotherapy apparatus having high success rate for defibrillation can be provided.

According to the electrotherapy apparatus of the third to seventh aspect of the invention, by controlling the electric parameters relating to the energy storage section, which vary corresponding to the delivering amount of the electric energy, the delivering energy can be controlled.

According to the electrotherapy apparatus of the eighth aspect of the invention, according to the patient parameter before the second phase waveform output and the electric parameters on the output electrode during the second phase waveform output, the electric power of the output energy can be controlled.

According to the electrotherapy apparatus of the ninth aspect of the invention, the biphasic defibrillator (electrotherapy apparatus) can be structured by one (capacitor) electric energy storage section, thereby, the second phase output waveform can be freely set.

According to the electrotherapy apparatus of the tenth aspect of the invention, by the simple control method, the second phase output waveform can be freely set.

According to the electrotherapy apparatus of the eleventh aspect of the invention, by the simple control method, the first phase and the second phase can be formed.

According to the electrotherapy apparatus of the twelfth aspect of the invention, by the electric control, the high speed opening/closing of each switch means can be conducted.

According to the electrotherapy apparatus of the thirteenth aspect of the invention, by controlling the shape of the pulse waveform, the apparatus is structured so that the necessary energy can be outputted within a constant time period, thereby, the effective energy can be delivered within the effective stimulation period.

According to the electrotherapy apparatus of the fourteenth aspect of the invention, by controlling so that the electric power becomes constant, independently of the value even when the impedance of the patient is low or high, the stimulation pulse having the effective energy amount can be applied.

According to the electrotherapy apparatus of the fifteenth to eighteenth aspect of the invention, when the electric parameters relating to the energy storage section which vary corresponding to the energy supply amount are controlled, the delivering energy can be controlled.

According to the electrotherapy apparatus of the nineteenth aspect of the invention, the electric power of the output energy can be controlled, according to the patient parameter before the output of the second phase waveform and the electric parameters on the output electrode during the output of the second phase waveform.

According to the electrotherapy apparatus of the twentieth aspect of the invention, when the switch in the electric circuit is continuously switching-operated by the pulse width modulation system, the electric power can be controlled so that the necessary energy is delivered.

According to the electrotherapy apparatus of the twenty first aspect of the invention, by controlling according to the stored reference curve, the stimulation pulse having the predetermined shape can be applied.

According to the electrotherapy apparatus of the twenty second to twenty third aspect of the invention, by controlling the electric parameters relating to the energy storage section which vary corresponding to the energy delivering amount according to the reference curve, the delivering energy can be controlled.

According to the electrotherapy apparatus of the twenty fourth aspect of the invention, by controlling so that the electric power becomes constant independently of the value even when the impedance of the patient is low or high, the stimulation pulse having the effective energy amount can be applied.

According to the electrotherapy apparatus of the twenty fifth aspect of the invention, the electric power of the output energy can be controlled, according to the patient parameter before the second phase waveform output and the electric parameters on the output electrode during the second phase waveform output.

According to the electrotherapy apparatus of the twenty sixth aspect of the invention, by controlling so that the electric power becomes constant independently of the value even when the impedance of the patient is low or high, the stimulation pulse having the effective energy amount can be applied.

According to the electrotherapy apparatus of the twenty seventh aspect of the invention, because the apparatus is structured in such a manner that the electric energy is supplied to the inductor, the shape of the waveform of the stimulation pulse can be controlled with the high degree of freedom.

According to the electrotherapy apparatus of the twenty eighth aspect of the invention, a predetermined energy amount in the energy stored in the electric energy storage section can be supplied to the inductor.

According to the electrotherapy apparatus of the twenty ninth aspect of the invention, by controlling the energy by supplying it to the inductor, even when the patient has the high impedance, the energy can be supplied while the voltage is made higher than the voltage value of the capacitor which is the electric energy storage section, at need.

According to the electrotherapy apparatus of the thirtieth aspect of the invention, by conducting the switching control, the energy stored in the capacitor is supplied once to the inductor, and then, can be supplied to output electrode.

According to the electrotherapy apparatus of the thirty first aspect of the invention, the switching is controlled by pulse width modulation control, therefore, the electric power can be controlled.

According to the electrotherapy apparatus of the thirty second aspect of the invention, by controlling so that the electric power becomes constant, independent of the value even when the impedance of the patient is low or high, the stimulation pulse having the effective energy amount can be applied.

According to the electrotherapy apparatus of the thirty third aspect of the invention, by controlling according to the stored reference curve, the stimulation pulse having the predetermined shape can be applied.

According to the electrotherapy apparatus of the thirty fourth to thirty fifth aspect of the invention, when the electric parameters relating to the energy storage section which vary corresponding to the energy delivering amount are controlled according to the reference curve, the delivering energy can be controlled.

According to the electrotherapy apparatus of the thirty sixth aspect of the invention, the apparatus has the charging circuit, thereby, when the energy is consumed by use, the apparatus can be used again.

According to the electrotherapy apparatus of the thirty seventh, or thirty eighth aspect of the invention, the biphasic electric stimulation pulse waveform can be freely outputted, thereby, the electrotherapy apparatus which is effective in terminating the fibrillation in the cardiac diseases, can be provided.

According to the electrotherapy apparatus of the thirty ninth aspect of the invention, the apparatus is an external type apparatus which can apply the stimulation pulse from the outside of the patient, thereby, the same apparatus can be used for the different patient.

According to the electric energy delivering method of the electrotherapy apparatus of the fortieth aspect of the invention, when the electric energy stored in the electric energy storage section is delivered to the patient in biphasic waveform, initially, the necessary electric energy is delivered in the first phase waveform, and next, the necessary electric energy is delivered from the remained energy, in the second phase waveform within a predetermined time period, thereby, predetermined electric energy can be delivered in the second phase waveform to the patient within the optimum time period for the defibrillation, without depending on the impedance of the patient.

According to the electric energy delivering method of the electrotherapy apparatus of the forty first aspect of the invention, when the electric energy stored in the electric energy storage section is repeatedly delivered onto the patient at the plurality of times alternately (multiphasic output waveform), by using the first phase waveform and the second phase waveform, by freely forming the shape of the second phase waveform without depending on the impedance of the patient, there is a possibility that the more effective defibrillation can be conducted.

In the electrotherapy apparatus shown by the present invention, when the power has been turned on, more than 98% of the energy stored in the energy storage section can be outputted, and the efficiency of use is very high, and this is advantageous for the reduction of the apparatus size and weight.

Further, because the energy stored in the energy storage section is used, it is not necessary to electrically isolate respectively and supply the energy, for the output of the second phase.

Further, because the instantaneous maximum electric power as the power source is determined by the internal resistance of the capacitor used in the energy storage section, it is not necessary to have the power source with the large electric power, and the reduction of size and weight can be realized.

In the electrotherapy apparatus shown by the present invention, in order to output the second phase waveform, as a means for storing the energy once, the inductor 105 is used (stored as the magnetic energy), thereby, even when the voltage is higher or lower than the voltage of the charging capacitor (energy storage section 104), the output can be conducted.

The feature of this invention is specifically effective for the external type defibrillator. This is for the reason that the impedance of the patient to which the external type defibrillator is applied, has the large distribution depending on the difference of the physical feature of each patient. However, this feature of the present invention could be also applied to the internal type defibrillator.

Because the electrotherapy apparatus of the present invention can outputs the biphasic waveform by one capacitor, additional circuit elements (switches of H bridge) are not necessary, thereby, the reduction of the size and weight can be realized. Further, by the electric power control, the voltage of the second phase can be set to the optimum value which is considered for the inherency of the impedance of the patient.

What is claimed is:

1. An electrotherapy apparatus comprising:
    an electric energy storage section generating a stimulation pulse;
    an output electrode for applying the stimulation pulse to a patient; and
    output control means for reversing polarity of the voltage outputted to the output electrode, outputting at least a first phase waveform and a second phase waveform to the output electrode, and controlling an amplitude and a duration of the second phase waveform irrespective of a duration of the first phase waveform.

2. An electrotherapy apparatus comprising:
    an electric energy storage section generating a stimulation pulse;
    an output electrode for applying the stimulation pulse to a patient; and
    output control means for reversing polarity of the voltage outputted to the output electrode, outputting at least a first phase waveform and a second phase waveform to the output electrode, and controlling independently a duration of the second chase waveform and an electric energy being delivered during the duration, within a range of energy remaining in the electric energy storage section.

3. An electrotherapy apparatus according to claim 2, wherein the output control means controls the electric power of the electric energy outputted from the output electrode to become constant without depending on a value of the impedance of the patient during the output period of the second phase waveform.

4. An electrotherapy apparatus according to claim 3, wherein the output control means controls the output so that the value relating to the voltage, which is lowered corresponding to the amount of the energy supplied from the electric energy storage section, changes corresponding to a function of the predetermined time period and the value relating to the voltage.

5. An electrotherapy apparatus according to claim 4, wherein the value relating to the voltage is one of a voltage value, voltage differential value, and voltage double differential value.

6. An electrotherapy apparatus according to claim 3, wherein the output control means controls the output so that the value relating to the current, which varies corresponding to the amount of the energy supplied from the electric energy storage section, changes corresponding to a function of the predetermined time period and the value relating to the current.

7. An electrotherapy apparatus according to claim 6, wherein the value relating to the current corresponds to one of a current value, current differential value, and current double differential value.

8. An electrotherapy apparatus according to claim 2 further comprising:
    patient parameter measuring means for measuring the patient parameter; and
    output electrode parameter measuring means for measuring the voltage generated between the output electrodes, or the current flowing to the output electrode;
    wherein the output control means controls the electric power of the electric energy to become constant without depending on a value of the patient impedance on the basis of the patient parameter measured by the patient parameter measuring means before the second phase waveform is outputted and a value, which relates to the voltage between the output electrodes or the current flowing to the output electrode, measured by the output electrode parameter measuring means during the output of the second phase waveform.

9. An electrotherapy apparatus according to claim 2, wherein the output control means comprises:
    an inductor;
    an electric energy storage section;
    first switch means for connecting the electric energy storage section,
    wherein when the waveform of the electric energy outputted from the output electrode is the first phase waveform, an inductor, electric energy storage section, the first switch means, the output electrode, patient, and at least, another output electrode are connected to form a closed circuit,
    wherein in the case where the waveform of the electric energy outputted from the output electrode is the second phase waveform, when the first switch means is closed, the inductor and the electric energy storage section without the patient form the closed circuit; and
    wherein when the first switch means is opened, the inductor and the electric energy storage section are electrically separated, and the electric energy is delivered from the inductor to the output electrode.

10. An electrotherapy apparatus according to claim 9, wherein the shape of the second phase waveform can be controlled by switching the first switch means.

11. An electrotherapy apparatus according to claim 9, wherein the output control means further comprises second switch means and third switch means for shaping the first phase waveform and the second phase waveform of the electric energy outputted from the output electrode.

12. An electrotherapy apparatus according to claim 11, wherein the first switch means, second switch means and third switch means comprise semiconductor switches.

13. An electrotherapy apparatus according to claim 2, further comprising:
    a charging circuit for charging the energy storage section.

14. An electrotherapy apparatus according to claim 2, wherein the apparatus is an external type defibrillator which applies the stimulation pulse onto the body surface of the patient.

* * * * *